United States Patent
Küber et al.

[11] Patent Number: 5,945,553
[45] Date of Patent: Aug. 31, 1999

[54] PROCESS FOR PREPARING A METHYLENE-BRIDGED BISCYCLOPENTADIENYL COMPOUND

[75] Inventors: Frank Küber, Oberursel; Michael Riedel, Essen; Berthold Schiemenz, Frankfurt, all of Germany

[73] Assignee: Targor GmbH, Germany

[21] Appl. No.: 08/928,208

[22] Filed: Sep. 12, 1997

[30] Foreign Application Priority Data

Sep. 16, 1996 [DE] Germany .............. 196 37 669

[51] Int. Cl.$^6$ .............. C07F 17/00; C07F 7/28; C07F 11/00

[52] U.S. Cl. .............. 556/53; 556/1; 556/43; 556/58; 526/160; 526/943; 502/103; 502/117; 502/152; 534/15; 585/361

[58] Field of Search ............... 556/1, 43, 53, 556/58; 526/160, 943; 502/103, 117, 152; 534/15; 585/361

[56] References Cited

U.S. PATENT DOCUMENTS

| | | | |
|---|---|---|---|
| 5,276,208 | 1/1994 | Winter et al. | 556/53 |
| 5,329,033 | 7/1994 | Spaleck et al. | 556/53 |
| 5,455,365 | 10/1995 | Winter et al. | 556/7 |
| 5,455,366 | 10/1995 | Rohrmann et al. | 556/8 |
| 5,670,681 | 9/1997 | Küber et al. | 556/53 |
| 5,693,836 | 12/1997 | Winter et al. | 556/11 |

FOREIGN PATENT DOCUMENTS 751 143  6/1996  European Pat. Off. .

OTHER PUBLICATIONS

Ewen et al., Makromol. Chem., Macromol. Symp., vol. 48/49, pp. 253–295, 1991.

E. Ghera et al., "Reactions of Active Methylene Compounds in Pyridine Solution. II. Aldol–type Reactions of Indene and Flourene", Journal of The American Chemical Society, (1960), pp. 4945–4952.

N.E. Schore et al., "Carbon–Carbon Bond Formation in Dinuclear Dialkyl Complexes, Reactions of [CpCo(CO)R]$_2$(R=CH$_3$,CH$_2$CH$_3$, CH$_2$CF$_3$) and (C$_{11}$H$_{10}$)(CO$_2$(CO)$_2$CH$_3$)$_2$ with Carbon Monoxide and Triphenylphosphine", Journal of the American Chemical Society, (1984) pp. 7451–7461.

*Primary Examiner*—Porfirio Nazario-Gonzalez
*Attorney, Agent, or Firm*—Connolly & Hutz

[57] ABSTRACT

Process for preparing a methylene-bridged cyclopentadienyl compound

The present invention relates to a process for preparing a methylene-bridged biscyclopentadienyl compound having the formula I

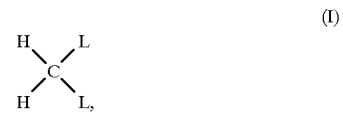

(I)

Where L are, independently of one another, identical or different and are each a cyclopentadienyl group, by reactin one or two cyclopentadienyl compounds LH with formaldehyde in monomeric, oligomeric or polymeric form or formaldehyde-generating reagents in the presence of at least one base and at least one phase transfer catalyst.

11 Claims, No Drawings

PROCESS FOR PREPARING A METHYLENE-BRIDGED BISCYCLOPENTADIENYL COMPOUND

DESCRIPTION

Process for preparing a methylene-bridged biscyclopentadienyl compound

The present invention relates to a process for preparing a methylene-bridged biscyclopentadienyl compound and the use of this process as a substep in the preparation of a methylene-bridged biscyclopentadienyl metallocene which can be used as a catalyst component, e.g. for the preparation of polyolefins.

The preparation of polyolefins in the presence of metallocenes in combination with aluminoxanes or other cocatalysts which, owing to their Lewis acidity, can convert the neutral metallocene into a cation and stabilize it is known from the literature.

Metallocenes and semi-sandwich complexes are of great interest not only in connection with the polymerization or oligomerization of olefins, but they can also be used as hydrogenation, epoxidation, isomerization and C-C coupling catalysts (Chem. Rev. 1992, 92, 965–994).

US-A4,892,851 and EP-A461 566 disclose carbon-bridged metallocenes. The synthesis of methylene-bridged metallocenes proceeds via the preparation of the methylene-bridged biscyclopentadienyl ligand system which has to be carried out in a plurality of stages and proceeds with only very low yields, cf. J. Am. Chem. Soc. 106, 1984, 7451 and Helv. Chim. Acta 48, 1965, 955.

It is also known from the literature that cyclopentadiene can be reacted directly cyclic ketones with addition of a base to give bridged biscyclopentadienyl ligands, cf. J. Chem. Research (S), 1992, 162. This synthesis proceeds with low yields and requires a complicated subsequent chromatographic purification.

It is an object of the present invention to provide a simple and economical process for preparing methylene-bridged biscyclopentadienyl compounds in high yields.

The object of the present invention is achieved by a process for preparing a methylene-bridged biscyclopentadienyl compound, which comprises reacting one or two cyclopentadienyl compounds LH with formaldehyde in monomeric, oligomeric or polymeric form or with formaldehyde-generating reagents in the presence of at least one base and at least one phase transfer catalyst.

The methylene-bridged biscyclopentadienyl compound has the formula I

(I)

where L are, independently of one another, identical or different and are each a cyclopentadienyl group.

The cyclopentadienyl groups L in formula I can be unsubstituted or substituted by, for example, $C_1$–$C_{20}$-radicals R such as $C_1$–$C_{20}$-alkyl, $C_6$–$C_{20}$-aryl, $C_6$–$C_{20}$-alkylaryl, $C_7$–$C_{20}$-arylalkyl or $C_2$–$C_{20}$-alkenyl. The radicals R can also form a ring system. The cyclopentadienyl groups L are identical or different, preferably identical.

Examples of substituted cyclopentadienyl groups L are:
tetramethylcyclopentadienyl, 3-methylcyclopentadienyl, 3-tert-butylcyclopentadienyl, methyl-tert-butylcyclopentadienyl,
isopropylcyclopentadienyl, dimethylcyclopentadienyl, trimethylcyclopentadienyl,
trimethylsilylcyclopentadienyl, trimethylethylcyclopentadienyl,
3-phenylcyclopentadienyl, diphenylcyclopentadienyl, indenyl, 2-methylindenyl,
2-ethylindenyl, 3-methylindenyl, 3-tert-butylindenyl, 3-trimethylsilylindenyl,
2-methyl-4-phenylindenyl, 2-ethyl-4-phenylindenyl, 2-methyl-4-naphthylindenyl,
2-methyl-4-isopropylindenyl, benzoindenyl, 2-methyl4,5-benzoindenyl,
2-methyl-α-acenaphthindenyl, 2-methyl-4,6-diisopropylindenyl, fluorenyl,
2-methylfluorenyl or 2,7-di-tert-butylfluorenyl.

Preferably, one or both cyclopentadienyl groups L are a substituted
cyclopentadienyl group, in particular an indenyl derivative such as indenyl,
2-methylindenyl, 2-ethylindenyl, 3-methylindenyl, 3-tert-butylindenyl,
3-trimethylsilylindenyl, 2-methyl-4-phenylindenyl, 2-ethyl-4-phenylindenyl,
2-methyl-4-naphthylindenyl, 2-methyl-4-isopropylindenyl, benzoindenyl,
2-methyl-4,5-benzoindenyl, 2-methyl-α-acenaphthindenyl or
2-methyl-4,6-diisopropylindenyl, or a fluorenyl derivative such as fluorenyl,
2-methylfluorenyl or 2, 7-di-tert-butylfluorenyl.

Examples of methylene-bridged biscyclopentadienyl compounds of the formula I are:
bisindenylmethane, bis(2-methylindenyl)methane,
bis(2-methyl4-phenylindenyl)methane, bis(2-ethyl-4-phenylindenyl)methane,
bis(2-methyl-4-naphthylindenyl)methane, bis(2-methyl-4,5-benzoindenyl)methane,
bis(methylcyclopentadienyl)methane, biscyclopentadienylmethane,
cyclopentadienyl-fluorenyl-methane, (3-methylcyclopentadienyl)-fluorenyl-methane,
indenyl-fluorenyl-methane, cyclopentadienyl-indenyl-methane, 3-tert-butylcyclopentadienyl-fluorenyl-methane.

Biscyclopentadienyl compounds of the formula I in which the two cyclopentadienyl groups L are identical are prepared using one cyclopentadienyl compound LH. To prepare biscyclopentadienyl compounds of the formula I in which the two cyclopentadienyl groups L are different, use is made of two cyclopentadienyl compounds LH which are different from one another. The cyclopentadienyl compounds LH used in the process of the invention can be unsubstituted or substituted by, for example, $C_1$–$C_{20}$-radicals R such as $C_1$–$C_{20}$-alkyl, $C_6$–$C_{20}$-aryl, $C_6$–$C_{20}$-alkylaryl, $C_7$–$C_{20}$-arylalkyl or $C_2$–$C_{20}$-alkenyl. The radicals R can also form a ring system.

Examples of substituted cyclopentadienyl compounds LH are:
tetramethylcyclopentadiene, methylcyclopentadiene, tert-butylcyclopentadiene,
methyl-tert-butylcyclopentadiene, isopropylcyclopentadiene, dimethylcyclopentadiene, trimethylcyclopentadiene, trimethylsilylcyclopentadiene,
trimethylethylcyclopentadiene, phenylcyclopentadiene, diphenylcyclopentadiene,
indene, 2-methylindene, 2-ethylindene, 3-methylindene, 3-tert-butylindene,
3-trimethylsilylindene, 2-methyl-4-phenylindene, 2-ethyl-4-phenylindene,
2-methyl-4-naphthylindene, 2-methyl-4-isopropylindene, benzoindene,
2-methyl-4,5-benzoindene, 2-methyl-α-acenaphthindene,
2-methyl-4,6-diisopropylindene, fluorene, 2-methylfluorene or
2, 7-di-tert-butylfluorene.

Preferably one or both of the cyclopentadienyl compounds LH used in the process of the invention are a substituted cyclopentadienyl compound, in particular an indene derivative such as indene, 2-methylindene, 2-ethylindene, 3-methyl indene, 3-tert-butylindene, 3-trimethylsilylindene, 2-methyl-4-phenylindene, 2-ethyl-4-phenylindene, 2-methyl-4-naphthylindene, 2-methyl-4-isopropylindene, benzoindene, 2-methyl-4,5-benzoindene, 2-methyl-α-acenaphthylindene or 2-methyl-4,6-diisopropylindene, or a fluorenyl derivative such as fluorene, 2-methylfluorene or 2,7-di-tert-butylfluorene.

The formaldehyde compounds used in the process of the invention are preferably formaldehyde, paraformaldehyde, formalin or formaldehyde-generating reagents such as urotropin.

Bases which can be used are, for example, hydroxides of groups Ia, IIa and IIIa of the Periodic Table of the Elements, e.g. LiOH, NaOH, KOH, RbOH, $Mg(OH)_2$, $Ca(OH)_2$ and $Sr(OH)_2$. Preference is given to using exactly one base, e.g. LiOH, NaOH or KOH.

Phase transfer catalysts which can be used are quaternary ammonium salts and phosphonium salts of the formula $[R^3_4Z]^+X^-$, where $R^3$ are identical or different and are each a hydrogen atom or a $C_1$–$C_{40}$-group such as a $C_1$–$C_{20}$-alkyl, $C_1$–$C_{10}$-alkoxy, $C_6$–$C_{20}$-aryl, $C_2$–$C_{12}$-alkenyl-, $C_7$–$C_{40}$-arylalkyl, $C_7$–$C_{40}$-alkylaryl, or $C_8$–$C_{40}$-arylalkenyl group, each of which can bear radicals such as $-NR^4_3$, $-SR^4_2$, $-SiR^4_3$ or $-OSiR^4_3$, where $R^4$ are identical or different and are each a halogen atom, a $C_1$–$C_{10}$-alkyl group or a $C_6$–$C_{10}$-aryl group, or two or more radicals $R^3$ together with the atoms connecting them can form a ring system which preferably contains from 4 to 40, particularly preferably from 5 to 15, carbon atoms, Z is nitrogen or phosphorus and $X^-$ is a halide, hydroxide, tetrahaloborate (e.g. tetrafluoroborate), hydrogensulfate, sulfate or hexahalophosphate (e.g. hexafluorophosphate).

Examples of compounds suitable as phase transfer catalysts are:
benzyltrimethylammonium chloride,
benzyltrimethylammonium hydroxide (in particular as an aqueous 40% strength solution),
hexadecyltrimethylammonium bromide,
hexadecyltrimethylammonium chloride (in particular as an aqueous 50% strength solution),
ethylhexadecyidimethylammonium bromide,
tetraethylammonium tetrafluoroborate,
tetraethylammonium bromide,
tetraethylammonium hydroxide (in particular as an aqueous 20% strength solution),
benzyltriethylammonium chloride,
benzyltriethylammonium hydroxide,
tetrapropylammonium bromide,
tetrabutylammonium chloride,
tetrabutylammonium fluoride trihydrate,
tetrabutylammonium tetrafluoroborate,
tetrabutylammonium hydrogensulfate,
tetrabutylammonium hydroxide (in particular as a 12.5% strength solution in methanol)
benzyltributylammonium bromide,
tetraoctylammonium bromide,
methyltrioctylammonium chloride,
tetrabutylphosphonium bromide,
tetrabutylphosphonium chloride,
tributylhexadecylphosphonium bromide,
ethyltrioctylphosphonium bromide,
butyltriphenylphosphonium chloride and tetraphenylphosphonium bromide.

Further compounds which can be used as phase transfer catalysts are crown compounds, in particular those of the formulae II, III and IV,

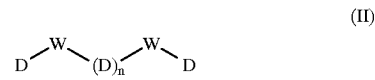
(II)

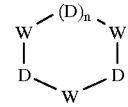
(III)

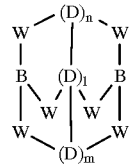
(IV)

where

D is S, O, $NR^5$, $PR^5$ and $R^5$ are identical or different and are each a hydrogen atom, a halogen atom, a $C_1$–$C_{40}$-group such as a $C_1$–$C_{20}$-alkyl, $C_1$–$C_{10}$-alkoxy, $C_6$–$C_{20}$-aryl, $C_2$–$C_{12}$-alkenyl, $C_7$–$C_{40}$-arylalkyl, $C_7$–$C_{40}$-alkylaryl or $C_8$–$C_{40}$-arylalkenyl group, each of which can bear radicals $-NR^6_3$, $-SR^6_2$, $-SiR^6_3$ or $-OSiR^6_3$, where $R^6$ are identical or different and are each a halogen atom, a $C_1$–$C_{10}$-alkyl group or a $C_6$–$C_{10}$-aryl group, W are identical or different and are $[R^7_2C]_n$, where $R^7$ are identical or different and are each a hydrogen atom, a halogen atom, a $C_1$–$C_{40}$-group such as a $C_1$–$C_{20}$-alkyl, $C_1$–$C_{10}$-alkoxy, $C_6$–$C_{20}$-aryl, $C_2$–$C_{12}$-alkenyl, $C_7$–$C_{40}$-arylalkyl, $C_7$–$C_{40}$-alkylaryl, or a $C_8$–$C_{40}$-arylalkenyl group, each of which can bear radicals $-NR^8_3$, $-SR^8_2$, $-SiR^8_3$ or $-OSiR^8_3$, where $R^8$ is a halogen atom, a $C_1$–$C_{10}$-alkyl group or a $C_6$–$C_{10}$-aryl group, or two or more radicals $R^7$ together with the atoms connecting them can form a ring system which preferably contains from 4 to 40, particularly preferably from 5 to 15, atoms, in particular carbon atoms, n, l and m are identical or different and are each an integer from 1 to 40, preferably from 1 to 5, and are preferably identical, and B are identical or different and are each an element of main group V of the Periodic Table, e.g. nitrogen or phosphorus.

Examples of crown ether compounds are:

12-crown-4, 15-crown-5, benzo-15-crown-5, 18-crown-6, decyl-18-crown-6, dibenzo-18-crown-6, dicyclohexyl-18-crown-8, dibenzo-24-crown-8, (+)-18-crown-6-tetracarboxylic acid, N-phenylaza-15-crown-5, ®Kryptofix 21, ®Kryptofix 22, ®Kryptofix 22 DD, ®Kryptofix 23, tris [2-(methoxyethoxy)ethyl]amine, ®Kryptofix 5, ®Kryptofix 111, ®Kryptofix 211, ®Kryptofix 221, ®Kryptofix 221 D, ®Kryptofix 222, ®Kryptofix 222 B (50% strength solution in toluene), ®Kryptofix 222

BB, ®Kryptofix 222 CC (50% strength solution in toluene), ®Kryptofix 222 D (50% strength solution in toluene), ®Kryptofix 221 B (polymer) and ®Kryptofix 222 B (polymer).

At least one phase transfer catalyst is used in the process of the invention. The concentration of the phase transfer catalyst can be from 0.1 to 100 mol%, based on the amount of cyclopentadienyl compound(s) LH used, particularly preferably from 1 to 20 mol%.

The process of the invention is carried out in a single-phase or multiphase system in the presence of at least one base and at least one phase transfer catalyst. The process of the invention is preferably carried out in a multiphase system, in particular in a two-phase system where one phase is an organic solvent, e.g. an aromatic solvent such as toluene or xylene or an aliphatic solvent such as tetrahydrofuran, hexane or dichloromethane, and the second phase is water. Particular preference is given to the two-phase systems toluene/water, dichloromethane/water and tetrahydrofuran/water. The concentration of base in the aqueous phase can be from 5 to 70% by weight, preferably from 25 to 60% by weight.

For the synthesis of methylene-bridged biscyclopentadienyl compounds having two identical cyclopentadienyl groups L, the cyclopentadienyl compound LH can be used in excess (based on the formaldehyde compound); preference is given to using from 2 to 3 equivalents of the cyclopentadienyl compound LH, based on the formaldehyde used. In the synthesis of methylene-bridged biscyclopentadienyl compounds having two different cyclopentadienyl groups L, use is made of two cyclopentadienyl compounds LH which are different from one another. In this synthesis, one of the two cyclopentadienyl compounds is first reacted with formaldehyde with the ratio of the two components being about 1:1. After a reaction time which can be from 30 minutes to 100 hours, preferably from 30 minutes to 20 hours, the second cyclopentadienyl compound is added.

The reaction temperature can be from 0° C. to 100° C., preferably from 0° C. to 30° C. The reaction times are generally from 30 minutes to 100 hours, preferably from 30 minutes to 20 hours.

The volume ratio of organic phase/water (e.g. toluene/water, dichloromethanetwater or tetrahydrofuran/water) can be from 10,000:1 to 1:50, preferably from 100:1 to 1:10, particularly preferably from 10:1 to 1:1.

Preferably, a mixture of the cyclopentadienyl compound LH and the formaldehyde compound is initially charged in the organic solvent and the aqueous phase in which both the base and the phase transfer catalyst are present is metered in. The reverse reaction sequence is also possible, i.e. formaldehyde can be added dropwise over a period of from 1 minute to 100 hours, preferably from 15 minutes to 4 hours, to the two-phase system (e.g. toluene/water, dichloromethane/water or tetrahydrofuran/water) in which the cyclopentadienyl compound LH, the base and the phase transfer catalyst are present.

The methylene-bridged biscyclopentadienyl compounds obtainable using the process of the invention can be obtained as double bond isomers.

The process of the invention is particularly notable for the fact that methylene-bridged biscyclopentadienyl compounds can be obtained in high yield in a simple, single-stage synthesis. The substitution pattern of the cyclopentadienyl groups L can be varied within a wide range.

The present invention further provides for the use of the process of the present invention as a substep of a process for preparing a methylene-bridged biscyclopentadienyl metallocene, in particular a carbon-bridged biscyclopentadienyl metallocene of the formula V

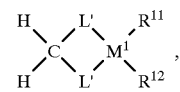

(V)

where

M$^1$ is an element of group IIIb, IVb, Vb or VIb of the Periodic Table of the Elements, in particular group IVb, L' are, independently of one another, identical or different and are each a cyclopentadienyl group, and R$^{11}$ and R$^{12}$ are identical or different and are each hydrogen, a halogen atom or a $C_1$–$C_{40}$-radical such as $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl, $C_8$–$C_{40}$-arylalkenyl, hydroxy, $NR^5{}_2$, where R$^5$ is $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl.

The cyclopentadienyl groups L' in formula V can be unsubstituted or substituted by, for example, $C_1$–$C_{20}$-radicals such as $C_1$–$C_{20}$-alkyl, $C_6$–$C_{20}$-aryl, $C_6$–$C_{20}$-alkylaryl, $C_7$–$C_{20}$-arylalkyl or $C_2$–$C_{20}$-alkenyl. The radicals R can also form a ring system. The cyclopentadienyl groups L are identical or different, preferably identical.

Examples of substituted cyclopentadienyl groups L' are:

tetramethylcyclopentadienyl, 3-methylcyclopentadienyl, 3-tert-butylcyclopentadienyl, methyl-tert-butylcyclopentadienyl, isopropylcyclopentadienyl, dimethylcyclopentadienyl, trimethylcyclopentadienyl, trimethylethylcyclopentadienyl, 3-phenylcyclopentadienyl, diphenylcyclopentadienyl, 3-trimethylsilylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthylindenyl, 2-methyl-4,6-diisopropylindenyl, fluorenyl, 2-methylfluorenyl, 2,7-diphenylfluorenyl or 2,7-di-tert-butylfluorenyl.

Preferably, one or both cyclopentadienyl groups L' is a substituted cyclopentadienyl group, in particular an indenyl derivative such as indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methylαc-acenaphthylindenyl or 2-methyl-4,6-diisopropylindenyl, or a fluorenyl derivative such as fluorenyl, 2-methylfluorenyl, 2,7-diphenyl-fluorenyl or 2,7-di-tert-butylfluorenyl.

$M^1$ is preferably an element of group IV of the Periodic Table of the Elements, e.g. titanium, zirconium or hafnium, in particular zirconium. $R^1$ and $R^2$ are identical or different, preferably identical, and are hydrogen, $C_1$–$C_{10}$-alkyl or $C_6$–$C_{14}$-aryl, in particular $C_1$–$C_5$-alkyl, and the radicals $R^{11}$ and $R^{12}$ are preferably identical and are each $C_1$–$C_4$-alkyl such as methyl or a halogen atom such as chlorine.

Examples of carbon-bridged biscyclopentadienyl metallocenes obtainable by the metallocene preparation process of the invention are:

methylene-bis(cyclopentadienyl)zirconium dichloride, methylene-bis(2,3,4,5-tetramethylcyclopentadienyl) zirconium dichloride, methylene-bis(2,3,4-trimethylcyclopentadienyl) zirconium dichloride, methylene-bis(1-indenyl)zirconium dichloride, methylene-bis(1-(2-methylindenyl)zirconium dichloride, methylene-bis(1-(4-phenylindenyl))zirconium dichloride, methylene-bis(1-(4-isopropylindenyl))zirconium dichloride, methylene-bis(1-(4-isopropylindenyl))hafnium dichloride, methylene-bis(1-(4,5-benzo indenyl)zirconium dichloride, methylene-bis(1-(4,5-benzoindenyl))hafnium dichloride, methylene-(1-indenyl)cyclopentadienylzirconium dichloride, methylene-(1-indenyl)(3-methylcyclopentadienyl) zirconium dichloride, methylene-(1-(4-isopropyl)indenyl) cyclopentadienylzirconium dichloride, methylene-(1-indenyl)cyclopentadienyltitanium dichloride, methylene-(1-indenyl)(3-methylcyclopentadienyl) titanium dichloride, methylene-(1-indenyl)(9-fluorenyl)zirconium dichloride, methylene-(9fluorenyl)(3-methylcyclopentadienyl) zirconjum dichloride, methylene-(9-fluorenyl)(3-tert-butylcyclopentadienyl) zirconium dichloride, methylene-(9-fluorenyl)cyclopentadienyl zirconium dichloride, methylene-(9-(2,7-di-ert-butyl)fluorenyl) cyclopentadienylzirconjum dichloride, Methylene-(9-(2,7-diphenyl)fluorenyl)cyclopentadienyl zirconium dichloride.

Preference is given to bisindenyl compounds bridged via the 1 positions of the indenyl ligands and having the formula methylenebis(1-Ind)$M^{11}R^{12}$, where Ind is an indenyl derivative and $M^1$, $R^{11}$ and $R^{12}$ are as defined in formula V. Indenyl derivatives Ind are, for example, indenyl which may bear $C_1$–$C_{20}$-hydrocarbon radicals such as $C_1$–$C_{20}$-alkyl, $C_6$–$C_{20}$-aryl, $C_6$–$C_{20}$-alkylaryl, $C_6$–$C_{20}$-arylalkyl or $C_2$–$C_{20}$-alkenyl and can also form a ring system, e.g. 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthyloindenyl, 2-methyl-4-isopropylindenyl, benzoindenyl, 2-methyle-4,5-benzoindenyl, 2-methy-α-acenaphthylindenyl or 2-methyl-4,6-diisopropylindenyl.

The present invention also provides a proc ess for preparing a methylene-bridged biscyclopentadienyl metallocene, comprising the steps:

a) reacting one or two cyclopentadienyl compounds LH with formaldehyde in monomeric, oligomeric or polymeric form or a formaldehyde-generating reagent in the presence of at least one base and at least one phase transfer catalyst to give a methylene-bridged biscyclopentadienyl compound, and b) reacting the methylene-bridged biscyclopentadienyl compound obtained in step a) with a metal compound $M^1X_p$, where $M^1$ is an element of group IIIb, IVb, Vb or VIb of the Periodic Table of the Elements, X is a $C_1$–$C_{40}$-radical such as $C_1$–$C_{10}$-alkyl or $NR^{13}_2$, where $R^{13}$ is a $C_1$–$C_{20}$-hydrocarbon radical such as $C_1$–$C_{10}$-alkyl or $C_6$–$C_{16}$-aryl, a halogen or a pseudohalogen and p is an integer from 0 to 4, under conditions under which the methylene-bridged biscyclopentadienyl compound obtained in step a) is complexed to give the methylene-bridged biscyclopentadienyl metallocene.

The second step (b) of the process for preparing the carbon-bridged biscyclopentadienyl metallocene can be carried out by methods known from the literature, e.g. AU-A-31478/89; J. Organomet. Chem. 1988, 342, 21 or EP-A-284 707, which are hereby expressly incorporated by reference. Preferably, the carbon-bridged biscyclopentadiene compound is first reacted with a compound of the formula $R^{14}M^2$, where $M^2$ is a metal of group Ia, IIa or IIIa of the Periodic Table of the Elements and $R^{14}$ is a $C_1$–$C_{20}$-hydrocarbon radical such as $C_1$–$C_{10}$-alkyl or $C_6$–$C_{14}$-aryl, and subsequently reacted with the metal compound $M^1X_p$. The reactions preferably take place in a suitable solvent, e.g. an aliphatic or aromatic solvent such as hexane or toluene, an ether solvent such as tetrahydrofuran or diethyl ether or in a halogenated hydrocarbon such as methylene chloride or o-dichlorobenzene. In the metal compound of the formula $M^1X_p$, $M^1$ is preferably an element of group IIIb of the Periodic Table of the Elements, X is preferably a halogen atom or $NR^{13}_2$ where $R^{13}$ is a $C_1$–$C_{10}$-hydrocarbon radical such as $C_1$–$C_{10}$-alkyl or $C_6$–$C_{10}$-aryl and p is preferably 4. The carbon-bridged biscyclopentadienyl compound can be used as a mixture of isomers.

Methylene-bridged biscyclopentadienyl metallocene halides of the formula V can be converted into the corresponding monoalkyl or dialkyl compounds by methods known from the literature for other carbon-bridged biscyclopentadienyl metallocene dihalides, e.g. by reaction with alkylating agents such as lithium alkyls, cf. J. Am. Chem. Soc. 1973, 95, 6263.

The methylene-bridged biscyclopentadienyl metallocenes of the formula V can be obtained as a mixture of the racemic form and the meso form. The separation of the isomeric forms, in particular the removal of the meso form, is known in principle, cf. AU-A-31478/89, EP-A-284 707 and J. Organomet. Chem. 342,1988, 21. The separation can be carried out, for example, by extraction or recrystallization using various solvents.

The process of the invention permits the simple preparation of methylene-bridged biscyclopentadienyl metallocenes in high yield.

The methylene-bridged biscyclopentadienyl metallocenes obtainable by the metallocene preparation process of the invention can, together with a cocatalyst, by used as highly active catalyst components, e.g. for the preparation of olefin polymers.

Olefins which can be polymerized are in particular those of the formula $R^a$—CH=CH—$R^b$, where $R^a$ and $R^b$ are identical or different and are each a hydrogen atom or a hydrocarbon radical having from 1 to 20 carbon atoms. $R^a$ and $R^b$ together with the carbon atoms connecting them can also form a ring. Examples of such olefins are ethylene, propylene, 1-butene, 1-hexene, 1-octene, 4-methyl-1-pentene, 1,3-butadiene, isoprene, norbornene, dimethanooctahydronaphthalene or norbornadiene. In particular, propylene and ethylene can be homopolymerized, ethylene can be copolymerized with a $C_3$–$C_{20}$-olefin and/or a $C_4$–$C_{20}$-diene or ethylene can be copolymerized with a cycloolefin.

The polymerization can be a homopolymerization or a copolymerization and can be carried out in solution, in suspension or in the gas phase, continuously or batchwise, in one or more stages at a temperature of from 0° C. to 200° C., preferably from 30° C. to 100° C.

In principle, a suitable cocatalyst in the polymerization is any compound which, owing to its Lewis acidity, can convert the neutral metallocene into a cation and stabilize the latter ("labile coordination"). Furthermore, the cocatalyst or the anion formed therefrom should undergo no further reactions with the cation formed, cf. EP-A427 697. The cocatalyst used is preferably an aluminum compound and/or boron compound.

As cocatalysts, preference is given to using aluminoxanes, cf. EP-A-129 368 and Polyhedron 9, 1990, 429. In place of or in addition to an aluminoxane, it is also possible to use boron compounds, in particular of the formulae $R_xNH_{4-x}BR_4'$, $R_xPH_{4-x}BR_4'$, $R_3CBR_4'$ or $BR_3'$, as cocatalyst. In these formulae, x is an integer from 1 to 4, preferably 3, the radicals R are identical or different, preferably identical, and are $C_1$–$C_{10}$-alkyl, $C_6$–$C_{18}$-aryl or 2 radicals R together with the atoms connecting them form a ring, and the radicals R' are identical or different, preferably identical, and are $C_6$–$C_{18}$-alkyl or $C_6$–$C_{18}$-aryl, which may be substituted by alkyl, haloalkyl or fluorine, cf. EP-A-277 003, EP-A-277 004, EP-A426 638 and EP-A-427 697.

It is possible to preactivate the metallocene using a cocatalyst, in particular an aluminoxane, before use in the polymerization reaction. This can significantly increase the polymerization activity. The preactivation of the metallocene is preferably carried out in solution. Here, the metallocene is preferably dissolved in a solution of the aluminoxane in an inert hydrocarbon. Suitable inert hydrocarbons are aliphatic or aromatic hydrocarbons. Preference is given to using toluene.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again prior to addition to the polymerization system.

Hydrogen can be added in the polymerization process as molecular weight regulator and/or to increase the catalyst activity. This enables low molecular weight polyolefins such as waxes to be obtained.

Preferably, the metallocene is reacted with the cocatalyst outside the polymerization reactor in a separate step using a suitable solvent. Application to a support can be carried out during this step.

In the process, a prepolymerization can be carried out with the aid of the metallocene. The prepolymerization is preferably carried out using the (or one of the) olefin(s) used in the polymerization.

The catalyst used for the olefin polymerization can be supported. The application to a support enables, for example, the particle morphology of the polymer produced to be controlled. The metallocene can be reacted first with the support and subsequently with the cocatalyst. The cocatalyst can also be supported first and subsequently reacted with the metallocene. It is also possible to support the reaction product of metallocene and cocatalyst. Suitable support materials are, for example, silica gels, aluminum oxides, solid aluminoxane or other inorganic support materials such as magnesium chloride. Another suitable support material is a polyolefin powder in finely divided form. The preparation of the supported cocatalyst can be carried out, for example, as described in EP-A-567 952.

The cocatalyst such as aluminoxane is preferably applied to a support such as silica gel, aluminum oxide, solid aluminoxane or another inorganic support material such as magnesium chloride or else a polyolefin powder in finely divided form and then reacted with the metallocene.

If the polymerization is carried out as a suspension or solution polymerization, an inert solvent customary for the Ziegler low-pressure process is used. For example, the polymerization is carried out in an aliphatic or cycloaliphatic hydrocarbon, for example propane, butane, hexane, heptane, isooctane, cyclohexane or methylcyclohexane. It is also possible to use a petroleum or hydrogenated diesel oil fraction. Toluene can also be used. Preference is given to carrying out the polymerization in the liquid monomer.

Use of hydrogen or increasing the polymerization temperature makes it possible to obtain low molecular weight polyolefins, e.g. waxes, whose hardness or melting point can be varied by means of the comonomer content. Selection of the polymerization process and the type(s) of comonomer and also amount(s) of comonomer enables olefin copolymers having elastomeric properties, e.g. ethylene-propylene-1,4-hexadiene terpolymers, to be prepared.

The present invention is illustrated by the following examples.

EXAMPLES

Example 1

Preparation of bis(1-indenyl)methane 100.0 g (0.86 mol) of indene were dissolved in 400 ml of toluene. 86.2 g (2.2 mol) of sodium hydroxide and 19.6 g (86 mmol) of triethylbenzylammonium chloride were subsequently added. The addition of 12.9 g (0.43 mol) of paraformaldehyde was carried out a little at a time over a period of 30 minutes. After a reaction time of 5 hours, the mixture was hydrolyzed with 200 ml of water. The aqueous phase was separated off and extracted twice with 100 ml each time of diethyl ether. The combined organic phases were dried over $MgSO_4$. The solvent was removed under reduced pressure and the crude product was purified by distillation in an oil pump vacuum. This gave 84.1 g of bis(1-indenyl)methane in a yield of 80% in the form of a yellow solid.

$^1$H-NMR (200 MHz, $CDCl_3$): 7.6–7.1 (m, 8H, arom. H), 6.22 (s, 2H, olefin, H), 3.85 (s, 2H, $CH_2$), 3.35 (d, 4H, $CH_2$). Mass spectrum: 244 M+, correct disintegration pattern.

Example 2

Preparation of methylenebis(1-indenyl)zirconium dichloride

A solution of 10 g (41 mmol) of bis(1-indenyl)methane in 50 ml of diethyl ether was admixed at room temperature under argon with 32.8 ml (82 mmol) of a 2.5 M butyllithium solution in hexane and stirred overnight. After addition of 40 ml of hexane, the beige suspension was filtered and the residue was washed with 20 ml of pentane. The dilithio salt was dried in an oil pump vacuum and then added at −78° C. to a suspension of 9.6 g (41 mmol) of ZrCl$_4$ in dichloromethane. The mixture was warmed to room temperature over a period of 1 hour and stirred further for 30 minutes at this temperature. After taking off the solvent, the orange-brown residue was extracted with 50 ml of toluene. Taking off the solvent gave 8.6 g (52%) of an orange powder. The ratio of racemate to meso form was determined as 2:1. Recrystallization from toluene gave 4.1 g (25%) of the pure racemate.

$^1$H-NMR (200 MHz, CDCl$_3$): 7.6–7.0 (m, 8H, arom. H), 6.58 (d, 2H, Cp-H), 5.96 (d, 2H, Cp-H), 4.79 (s, 2H, CH$_2$).

Mass spectrum: 402 M+, correct disintegration pattern.

Example 3

Preparation of bis(1-(2-methyl)indenyl)methane 100 g (0.77 mol) of 2-methylindene were dissolved in 400 ml of toluene. A solution of 86.2 g (2.2 mol) of sodium hydroxide and 19.6 g (86 mmol) of triethylbenzylammonium chloride in 86.2 ml of water (50% strength NaOH solution) was subsequently added. The addition of 31.2 g (0.39 mmol) of formalin (37% strength) was carried out dropwise over a period of 30 minutes. After a reaction time of 5 hours, the mixture was hydrolyzed with 100 ml of H$_2$O. The aqueous phase was separated off, extracted twice with 100 ml each time of diethyl ether and the combined organic phases were dried over MgSO$_4$. The solvent was removed in an oil pump vacuum and the crude product was distilled at 10$^{-1}$ mbar. This gave 40.4 g of bis-(1-(2-methyl)indenyl) methane in a yield of 38% in the form of a yellow solid.

$^1$H-NMR (200 MHz, CDCl$_3$): 7.6–6.9 (m, 8H,arom. H), 6.27 (s, 2H, olefin, H), 3.88 (s, 2H, CH$_2$), 3.37 (s, 2H, CH$_2$), 1.61 (s, 3H, CH$_3$).

Mass spectrum: 272 M+, correct disintegration pattern.

Example 4

Preparation of methylenebis(1-(2-methylindenyl)zirconium dichloride

A solution of 11.1 g (40 mmol) of bis(1-(2-methyl) indenyl)methane in 50 ml of toluene and 1.6 ml (80 mmol) of diethyl ether were admixed at room temperature under argon with 30 ml (80 mmol) of a 20% strength n-butyllithium solution in toluene and stirred for 16 hours. The suspension obtained was cooled to −30° C. and 9.3 g (40 mmol) of zirconium tetrachloride were then added. The mixture was slowly warmed to 30° C. over a period of 1 hour and stirred further for 3 hours at this temperature. After addition of 5 g of Celite, the mixture was filtered and the residue was washed twice with about 30 ml of toluene. The combined filtrates were evaporated to 40 ml in an oil pump vacuum and the concentrated solution was cooled to −30° C. The orange solid which precipitated was filtered off, washed with a little toluene and dried in an oil pump vacuum. This gave 6.3 g (36%) of an orange powder. The ratio of the racemate to the meso form was determined as 16:1.

$^1$H-NMR (200 MHz, CDCl$_3$): 7.76.95 (m, 8H, arom. H), 6.55 (s, 2H, Cp-H), 4.85 (s, 2H, CH$_2$), 2.26 (s, 6H, CH$_3$). Mass spectrum: 432 M+, correct disintegration pattern.

Example 5

Preparation of bis(9-fluorenyl)methane 16.6 g (0.1 mol) of fluorene were dissolved in 150 ml of toluene. 8.0 g (0.2 mol) of sodium hydroxide and 1.61 g (5 mmol) of tetrabutylammonium bromide were subsequently added. After 1 hour, 1.5 g (0.05 mol) of paraformaldehyde were added a little at a time over a period of 30 minutes. After a reaction time of 6 hours, the reaction mixture was hydrolyzed with a mixture of 200 ml of water and 12 g (0.2 mol) of glacial acetic acid. The aqueous phase was separated off and extracted twice with 100 ml each time of methylene chloride. The combined organic phases were dried over MgSO$_4$, filtered and evaporated under reduced pressure to 50 ml. Cooling to 0° C. and filtration gave 8.5 g (49%) of bis(9-fluorenyl)methane as a colorless powder.

$^1$H-NMR (200 MHz, CDCl$_3$): 7.9–6.8 (m, 16H,arom. H), 4.42 (t, 2H, H-Flu), 2.80 (d, 2H, CH$_2$). Mass spectrum: 344 M+, correct disintegration pattern.

Example 6

Preparation of methylenebis(9-fluorenyl)zirconium dichloride

A solution of 3.44 g (10 mmol) of bis(9-fluorenyl) methane in 70 ml of diethyl ether was admixed at 22° C. with 8 ml (20 mmol) of n-butyllithium solution (20% strength in toluene). The suspension obtained after stirring for 16 hours was cooled to −30° C. and 2.3 g (10 mmol) of zirconium tetrachloride were then added. After 3 hours, the mixture was filtered, the black residue was washed 4 times with 20 ml each time of hot toluene and dried in an oil pump vacuum. This gave 4.6 g of a green powder which is insoluble in all the usual organic solvents and consists essentially of methylenebis(9-fluorenyl)zirconium dichloride and lithium chloride. Mass spectrum: 502 M+, correct disintegration pattern.

Example 7

Polymerization 10 mg (0.023 mmol) of methylenebis(1-(2-methyl) indenyl)zirconium dichloride are suspended in 1 cm$^3$ of 30% strength (4.81 mmol) methylaluminoxane solution in toluene.

In parallel thereto, a dry 16 dm$^3$ reactor was first flushed with nitrogen and subsequently with propylene and was charged with 10 dm$^3$ of liquid propylene. 3 cm$^3$ of triisobutylaluminum (undiluted, 12 mmol) were then diluted with 30 cm$^3$ of hexane and introduced into the reactor, and the mixture was stirred at 30° C. for 15 minutes. The catalyst suspension was subsequently introduced into the reactor. The reaction mixture was heated to the polymerization temperature of 50° C. (or 70° C.) at 4° C./min and the polymerization system was held at 50° C. (or 70° C.) for 1 hour by cooling. The polymerization was stopped by venting the residual propylene. The polymer was dried in a vacuum drying oven and had the following properties:

Polymerization at 50° C.: 30 kg of PP/g of met xh, VN: 14 cm$^3$/g, m.p.: 106° C., M$_w$: 6530 g/mol, M$_w$/M$_n$: 2.0

Polymerization at 70° C.: 68 kg of PP/g of met xh, VN: 14 cm$^3$/g, m.p.: 100° C., M$_w$: 6140 g/mol, M$_w$/M$_n$: 2.0.

We claim:

1. A process for preparing a methylene-bridged biscyclopentadienyl compound having the formula I

where L are, independently of one another, identical or different and are each a cyclopentadienyl group, by reacting one or two cyclopentadienyl compounds LH with formaldehyde in monomeric, oligomeric or polymeric form or formaldehyde-generating reagents in the presence of at least one base and at least one phase transfer catalyst.

2. The process as claimed in claim 1, wherein the process is carried out in a multiphase system.

3. The process as claimed in claim 1, wherein the process is carried in a two-phase system which comprises an organic solvent and water.

4. The process as claimed in claim 1, wherein the base is a hydroxide of group Ia, IIa or IIIa of the Periodic Table of the Elements.

5. The process as claimed in claim 1, wherein the phase transfer catalyst is a quaternary ammonium salt, a quaternary phosphonium salt or a crown compound.

6. The process as claimed in claim 1, wherein, in formula I, one or both cyclopentadienyl groups L are substituted cyclopentadienyl groups.

7. A process for preparing a methylene-bridged cyclopentadienyl metallocene, comprising the steps
a) preparing a methylene-bridged biscyclopentadienyl compound by the process as claimed in one or more of claims 1 to 6, and
b) reacting the carbon-bridged biscyclopentadienyl compound obtained in step a) with a metal compound $M^1X_p$, where $M^1$ is an element of group IIIb, IVb, Vb or VIb of the Periodic Table of the Elements, X is a $C_1$–$C_{40}$-radical, a halogen or a pseudohalogen and p is an integer from 0 to 4, under conditions under which the methylene-bridged biscyclopentadienyl compound obtained in step a) is complexed to give the methylene-bridged biscyclopentadienyl metallocene.

8. The process as claimed in claim 7, wherein $M^1$ is an element of group IVb.

9. The process as claimed in claim 7, wherein said methylene-bridge biscyclopentadienyl is of the formula V

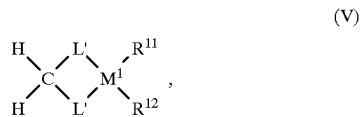

(V)

where
$M^1$ is an element of group IIIb, IVb, Vb or VIb of the Periodic Table of the Elements,
L' are, independently of one another, identical or different and are each a cyclopentadienyl group, and
$R^{11}$ and $R^{12}$ are identical or different and are each hydrogen, a halogen atom or a $C_1$–$C_{40}$-radical such as $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl, $C_8$–$C_{40}$-arylalkenyl, hydroxy, $NR^5{}_2$, where $R^5$ is $C_1$–$C_{10}$-alkyl, $C_1$–$C_{10}$-alkoxy, $C_6$–$C_{14}$-aryl, $C_6$–$C_{14}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl.

10. The process as claimed in claim 9, wherein $M^1$ is an element of group IVb, of the Periodic Table of Elements, L' are identical or different and are unsubstituted cyclopentadienyl, tetramethylcyclopentadienyl, 3-methylcyclopentadienyl, 3-tert-butylcyclopentadienyl, methyl-tertbutylcyclopentadienyl, isopropylcyclopentadienyl, dimethylcyclopentadienyl, trimethylcyclopentadienyl, trimethylethylcyclopentadienyl, 3-phenylcyclopentadienyl, diphenylcyclopentadienyl, 3-trimethylsilylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, benzoindenyl, 2-methyl-4,5-benzoindenyl, 2-methyl-α-acenaphthylindenyl, 2-methyl-4,6-diisopropylindenyl, fluorenyl, 2-methylfluorenyl, 2,7-diphenylfluorenyl or 2,7-di-tert-butylfluorenyl and
$R^{11}$ and $R^{12}$ are identical or different and are $C_1$–$C_4$-alkyl or a halogen atom.

11. The process as claimed in claim 10, wherein said methylene-bridge biscyclopentadienyl metallocene is
methylene-bis(cyclopentadienyl)zirconium dichloride,
methylene-bis(2,3,4,5-tetramethylcyclopentadienyl) zirconium dichloride,
methylene-bis(2,3,4-trimethylcyclopentadienyl) zirconium dichloride,
methylene-bis(1-indenyl)zirconium dichloride,
methylene-bis(1-(2-methylindenyl)zirconium dichloride,
methylene-bis(1-(4-phenylindenyl))zirconium dichloride,
methylene-bis(1-(4-isopropylindenyl))zirconium dichloride,
methylene-bis(1-(4-isopropylindenyl))hafnium dichloride,
methylene-bis(1-(4,5-benzoindenyl)zirconium dichioride,
methylene-bis(1-(4,5-benzoindenyl))hafnium dichloride,
methylene-(1-indenyl)cyclopentadienylzirconium dichloride,
methylene-(1-indenyl)(3-methylcyclopentadienyl) zirconium dichioride,
methylene-(1-(4-isopropyl)indenyl) cyclopentadienylzirconium dichloride,
methylene-(1-indenyl)cyclopentadienyltitanium dichioride,
methylene-(1-indenyl)(3-methylcyclopentadienyl) titanium dichloride,
methylene-(1-indenyl)(9-fluorenyl)zirconium dichloride,
methylene-(9-fluorenyl)(3-methylcyclopentadienyl) zirconium dichloride,
methylene-(9-luorenyl)(34ert-butylcyclopentadienyl) zirconium dichloride,
methylene-(9-fluorenyl)cyclo pentadienylzirconium dichloride,
methylene-(9-(2,7-di-tert-butyl)fluorenyl) cyclopentadienylzirconium dichloride or
methylene-(9-(2,7-diphenyl)fluorenyl) cyclopentadienylzirconium dichloride.

* * * * *